United States Patent [19]

Kotani et al.

[11] Patent Number: 5,024,951
[45] Date of Patent: Jun. 18, 1991

[54] METHOD OF CALIBRATING A SHEET TYPE ELECTRODE

[75] Inventors: Haruo Kotani; Katsuhiko Tomita, both of Kyoto, Japan

[73] Assignee: Horiba, Ltd., Kyoto, Japan

[21] Appl. No.: 276,779

[22] Filed: Nov. 28, 1988

Related U.S. Application Data

[62] Division of Ser. No. 124,629, Nov. 24, 1987, abandoned.

[51] Int. Cl.$^5$ .............................................. G01N 33/00
[52] U.S. Cl. ........................................ 436/8; 204/408
[58] Field of Search .................................. 436/8–19; 204/414, 420, 435, 408; 252/408.1; 128/635

[56] References Cited

U.S. PATENT DOCUMENTS 4,649,121 3/1987 Ismail et al. ........................ 436/14
4,816,132 3/1989 Kotani et al. ...................... 204/408

Primary Examiner—Thomas Wallen
Attorney, Agent, or Firm—Price, Gess & Ubell

[57] ABSTRACT

A method of measuring an ion-concentration characterized by a sample absorbed in an easily absorbing solution material and the absorbing material is brought into contact with a measuring portion to measure an ion-concentration 10/90 in the sample so that a highly accurate measurement can be achieved even though a quantity of the sample is small. In addition, the desired measurement can be carried out without using any instruments for sampling and needing any complicated pretreatments. A sheet for use in the calibration of an ion-concentration 10/90 measuring device characterized by a calibrating buffer solution absorbed in a chemically stabilized, hygroscopic, water-absorbing sheet eluting no ions and then the water-absorbing sheet is dried.

4 Claims, 6 Drawing Sheets

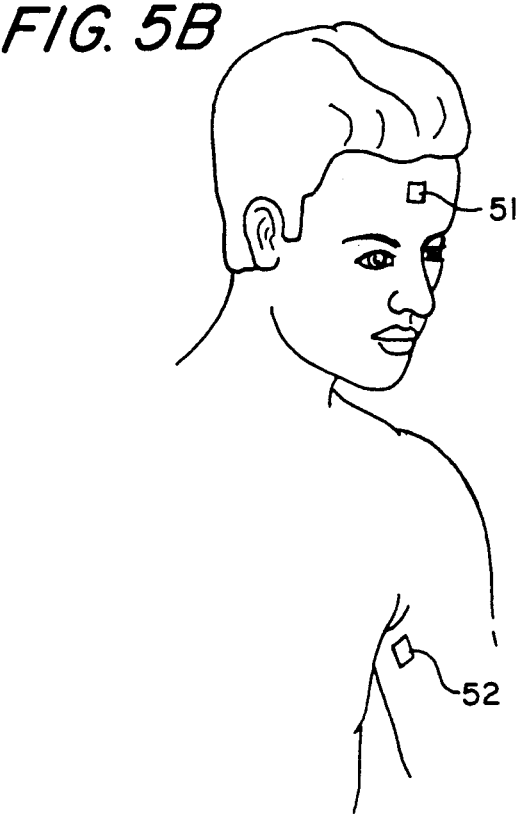
FIG. 5B
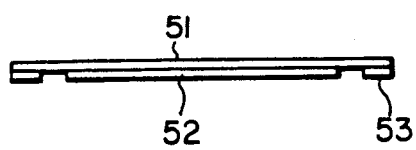
FIG. 5A
FIG. 6A
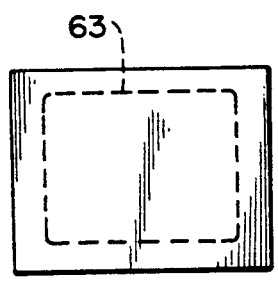
FIG. 6B
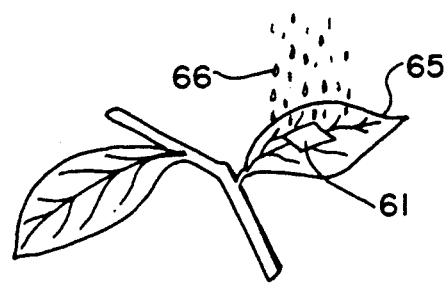
FIG. 6
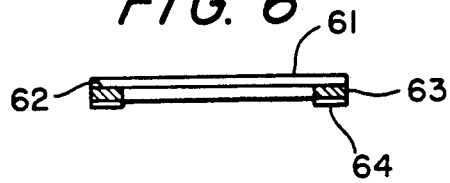

METHOD OF CALIBRATING A SHEET TYPE ELECTRODE

This is a division of application Ser. No. 124,629, filed Nov. 24, 1987 now abandoned.

BACKGROUND OF THE INVENTION

1. Field of the Invention

The present invention generally relates to methods of measuring ion-concentration and the like and a calibrating sheet as well as a calibrating method of measuring devices used therein.

2. Description of the Prior Art

In the case where various ion-concentrations, such as quantities of dissolved oxygen, conductivities and the like (hereinafter, ion-concentrations and the like) are in infinitesimal quantities of a liquid secreted from a living body and are measured, different sampling jigs have been used for every item to be measured to obtain a sample for the measurement.

For example, to sample saliva, a cotton roll has been put in an oral cavity to impregnate the cotton roll with the saliva. Then, the cotton roll has been subjected to centrifugal separation by means of a centrifugal separator to obtain saliva without impurities. To sample saliva from glandula parotis, a cup has been put on a mucous membrane of an oral cavity in an adhered manner to obtain an appointed saliva (prior art 1).

To sample sweat emanating from a surface of a body, a quantitative test method (QPIT method) has been used. For example, sweat from an arm has been absorbed by a filter paper and diluted to measure an ion-concentration. Or, an ion electrode and a conductivity electrode have been directly pressed against a skin perspiring sweat (prior art 2).

In addition, as to an ion-concentration, in particular, pH of a skin, an electrode whose glass electrode surface alone is a flat surface has been pressed against a skin (prior art 3).

Furthermore, a deterioration test of iron and steel subjected to a pretreatment for painting, painting of cars, painting of buildings, plated articles and the like may be carried out. For example, in the measurement of pH, pNa, pCl, conductivity and the like of contaminating substances adhered to a painted film on iron and steel, contaminating substances have been sampled by mopping up the painted film of an appointed area in an appointed direction and number of times by means of a gauze. The gauze was boiled in distilled water and impregnated with it; and by the use of a clean glove, the gauze is boiled in distilled water for one hour, and a total volume of 500 ml is made to obtain an appointed sample (prior art 4).

However, the prior arts have the following disadvantages, respectively.

That is to say, according to the prior arts 1, 2 and 4, to obtain a sample to be measured, considerable instruments are required and pretreatment is necessary. In short, a disadvantage is that great time and labor are required in the measurement. In the case of prior art 3, the measurement can be achieved only for a portion of skin capable of direct touching, and a quantity of KCl leaked is increased, whereby the measured result cannot be distinguished from an influence by a solution.

In addition, merely a small amount of sample to be measured can be sampled, whereby it is difficult to achieve an accurate measurement of the items to be measured.

In the event that an electrode of a pH meter is calibrated, five kinds of standard buffer solution have been used, for which their preparation methods are provided by JIS. That is to say, the standard solution having pH of 1.68, 4.01, 6.86, 9.18 and 10.02, respectively, at 25° C. has been used as a calibrating solution. The five kinds of standard buffer solution include an oxalate standard solution [0.05 M-aqueous solution of potassium tetra oxalate $KH_3(C_2O_4)_2 \cdot 2H_2O$], a phthalate standard solution [0.05 M-aqueous solution of potassium hydrogen phthalate $C_6H_4(COOK)(COOH)$], a neutral phosphate standard solution [0.025 M-aqueous solution of mono potassium phosphate $KH_2PO_4$ + 0.025 M-aqueous solution of disodium phosphate $Na_2HPO_4$], a borate standard solution [0.01 M-aqueous solution of sodium borate (borax) $Na_2B_4O_7 \cdot 10H_2O$], and a carbonate standard solution [0.025 M-aqueous solution of sodium hydrogen carbonate $NaHCO_3$ + 0.025 M-aqueous solution of sodium carbonate $Na_2CO_3$].

Pure water having a conductivity of $2 \times 10^{-6} \Omega^{-1} cm^{-1}$ (at 25° C.) or less has also been used in the preparation of the standard buffer solutions. For example, the oxalate standard solution is prepared by dissolving 12.71 g of potassium tetra oxalate (JIS K8474, for use in the measurement of pH) in the pure water so as to be 1 liter in total.

FIG. 15 shows a procedure of the conventional calibrating method. Referring to FIG. 15, "preservation" means that the prepared standard solution is preserved in a bottle made of high quality glass or polyethylene in a sealed manner. A calibrating solution including the standard solutions, which are prepared and preserved in the above described manner, in the form of a set is commercially sold as an accessory of a pH meter.

Since a pH meter can achieve a measurement with accuracy when calibrated, in the measurement of pH it is necessary to carry out a calibration if the need arises. Accordingly, the above described calibrating solution is indispensable. Setting aside measurements in the laboratory, where a measurement is conducted out of doors and on fields, it is necessary to carry the above described set of calibrating solutions and washings together with the pH meter. Attendant disadvantages are that the apparatus is remarkably bulky, the calibrating operation is remarkably difficult to conduct out of doors, and the calibration is difficult to accurately carry out. In short, the measurement of pH has been difficult to accurately carry out.

SUMMARY OF THE INVENTION

It is an object of the present invention to provide a method of measuring an ion-concentration and the like with high accuracy, even though merely a small amount of sample to be measured can be sampled, and a desired measurement can be achieved without using any instruments for sampling and needing a complicated pretreatment.

It is another object of the present invention to provide a sheet for use in the calibration which is handy and easy to use, and a calibrating method capable of easily calibrating in the measurement.

To achieve the above described objects, a method of measuring an ion-concentration and the like, according to the present invention, is characterized by an ion-concentration and the like in a sample being measured by impregnating an easily absorbing solution material with a sample and bringing the material into contact with a measuring portion.

According to a method of the present invention for measuring an ion-concentration and the like, a sample is absorbed in an easily absorbing solution material and the absorbing material is brought into contact with a measuring portion to measure an ion-concentration and the like in the sample so that a highly accurate measurement can be achieved even though a quantity of the sample is small. In addition, the desired measurement can be carried out without using any instruments for sampling and needing any complicated pretreatments.

A sheet for use in the calibration of an ion-concentration (and the like) measuring device, according to the present invention, is characterized by a calibrating buffer solution absorbed in a chemically stabilized, hygroscopic, water-absorbing sheet eluting no ions and then the water-absorbing sheet is dried.

Since a sheet for use in the calibration of an ion-concentration (and the like) measuring device, according to the present invention, is obtained by absorbing the calibrating buffer solution in the water-absorbing sheet and then drying the water-absorbing sheet, the sheet can be preserved in the form of a solid sheet. Accordingly, the apparatus is not bulky but is handy. In addition, it is sheet-like, so that it is easy to handle.

A method of calibrating an ion-concentration (and the like) measuring device according to the present invention is characterized by having a sheet for use in calibration which is obtained by absorbing a calibrating buffer solution in .a chemically stabilized, hygroscopic, water-absorbing sheet eluting no ions. The water-absorbing sheet is then dried and brought into contact with an electrode of the ion-concentration (and the like) measuring device. An appointed calibration is carried out by adding an appointed quantity of pure water drop by drop to the sheet for use in the calibration.

Since, in the method of calibrating an ion-concentration (and the like) measuring device according to the present invention, it is necessary to only bring the sheet for use in the calibration into contact with an electrode of the ion-concentration (and the like) measuring device and add an appointed quantity of pure water drop by drop to the sheet for use in the calibration, simple and secure calibration can be achieved.

BRIEF DESCRIPTION OF THE DRAWINGS

The preferred embodiments of the present invention are shown in the drawings, in which:

FIG. 5(A), (B) is a diagram showing a case where an ion-concentration of sweat is measured;

FIG. 6(A), (B) is a diagram showing a case where an ion-concentration of rain is measured;

DESCRIPTION OF THE PREFERRED EMBODIMENTS

The preferred embodiments of the present invention will be described below with reference to the drawings.

Figure 1:
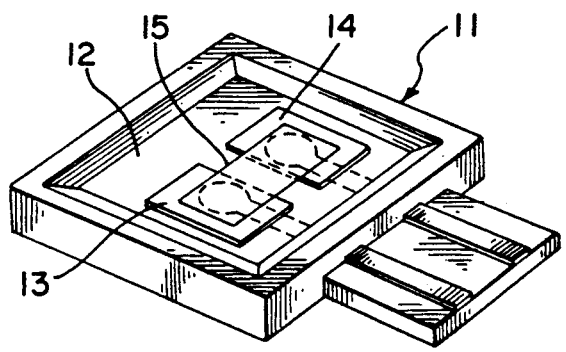
FIG. 1 is a perspective view showing one example of an ion-concentration measuring composite electrode used in the practice of a method according to the present invention.

FIG. 1 shows one example of a sheet type ion-concentration measuring composite electrode and an easily absorbing solution material used in the practice of a method according to the present invention. Reference numeral 11 designates a sheet type ion-concentration measuring composite electrode in which a measuring portion 12 is provided. The measuring portion 12 has a selective ion-response membrane a part of a measuring electrode 13 and a liquid junction membrane, which is formed of inorganic sintered porous materials or organic high molecular porous materials impregnated with KCl, as part of a reference electrode 14.

A sheet type ion-concentration measuring composite electrode constructed in this manner was applied for patent by the present assignee (Horiba Ltd.) on Nov. 28, 1986 in Japan, see U.S. Pat. No. 4,816,132.

In addition, referring again to FIG. 1, reference numeral 15 designates an easily absorbing solution material extending over the measuring electrode 13 and the reference electrode 14. The material 15 easily absorbs a solution, is chemically stabilized, flexible, and emanates no interferential ingredient against an object or item to be measured. The material 15 includes, for example, a sponge, absorbent cotton, neutral paper, porous glass, glass fiber and the like, and can be used in various shapes, as found in the following preferred embodiments.

FIGS. 2 to 6 show a measuring method in which a sample to be measured is liquid.

Figure 2A:
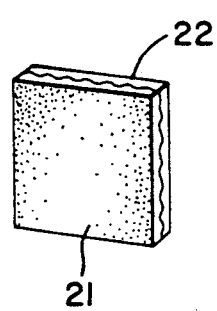
FIG. 2(A), (B), (C) is a diagram showing a case where an ion-concentration of saliva is measured.
Figure 2B:
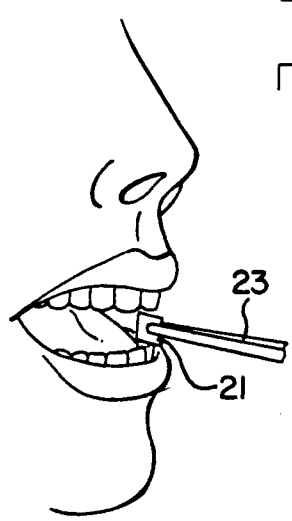
Figure 2C:
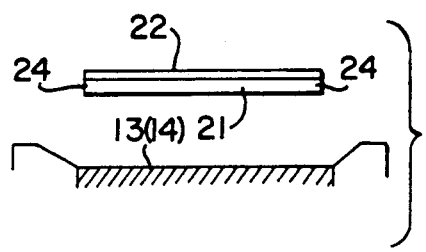

FIG. 2 shows a case where an ion-concentration in saliva is measured. As shown in FIG. 2(A), an assembly (15 mm × 15 mm) has a sheet type absorbing material 21 and an evaporation-inhibiting high molecular sheet 22 in piles. The assembly is adhered to a portion of each gland perspiring saliva for about ten and several seconds while holding it by means of a pair of tweezers 23. Thereby, the assembly absorbs saliva in the absorbing material 21 [FIG. 2(B)]. And then, the assembly is placed on the measuring portion 12 so that a side of the absorbing material 21 may be brought into contact with a side of the electrode 13(14) to be able to measure pH, pNa, pK, pCl, conductivity and the like of saliva [FIG. 2(C)].

In addition, reference numeral 24 designates a sealing portion to be sealed by heat or ultrasonic wave.

In this case, a sample of saliva of several microliters to several tens of microliters is sufficient in quantity for measurement. Advantages are that few instruments for obtaining a sample are required, and pretreatment is not required, which is different from the prior art 1.

It is preferable that, for secretions from a living body, a particularly small amount of tear, mucous, sperm, vaginal liquid and the like is sampled by means of a thin high molecular nonwoven fabric. This fabric is about several microns to 100 microns and acts as the absorbing material over a wide area.

FIG. 3 shows the sampling of a tear. Specifically FIG. 3(A) depicts a tear 31 when an eye lotion is being added drop by drop and a tear 33 on a contact lens 32. Since only a piece of thin film nonwoven sheet 34 is difficult to handle after the sampling of a tear, a frame member 35 is provided on a back side of the sheet 34 [FIG. 3(B)]. Alternatively, a multi-layer construction [FIG. 3(C)] having a hydrophilic absorbing sheet 34a and a hydrophobic absorbing sheet 34b is given to the sheet 34 to prevent evaporation from the hydrophobic surface and improve adhesion to the electrode 13 (14) [FIG. 3(D)].

In addition, reference numeral 36 designates a sealing portion to be sealed by heat or ultrasonic wave.

FIG. 4 shows a sampling in a case where pH within a vagina and sperm is measured.

Figure 4A:
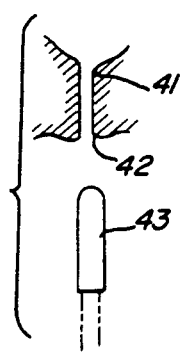
FIG. 4(A), (B), (C), (D), (E) is a diagram showing a case where an ion-concentration of vaginal liquid and sperm is measured.

As shown in FIG. 4(A), to measure pH in a circumference 41 of a womb and in a circumference 42 of a vagina, which are effective for the discrimination between sexes of an embryo, a fingerstall 43 is provided. The fingerstall 43 is formed of an absorbing material, put on a clean finger, and then inserted into the vagina to adhere vaginal liquid to an external circumference of the fingerstall 43.

Figure 4B:
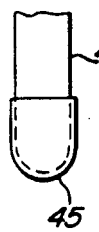
Figure 4C:
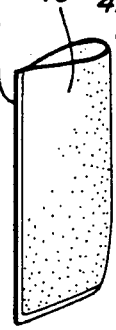
Figure 4D:
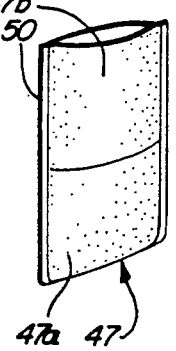
Figure 4E:
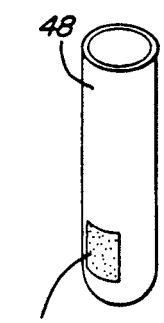

In addition, FIG. 4(B) shows a sack 45 formed of an absorbing material for sampling sperm from a penis 44. FIGS. 4(C), (D), (E) show an absorbing material suitable for sampling from merely the circumference of the womb. In particular, FIG. 4(C) shows a sack 46 formed of an absorbing material as a whole. FIG. 4(D) shows a sack 47 having a pointed end portion which is formed of an absorbing material 47a and a base end portion which is formed of an evaporation-inhibiting high molecular sheet 47b. FIG. 4(E) shows a sack 48 formed, for example, of rubber and provided with an absorbing material 49 at a part of a pointed end portion thereof.

In addition, reference numeral 50 designates a sealing portion to be sealed by heat or ultrasonic wave.

FIG. 5 shows a case where sweat is sampled. In FIG. 5(A), an evaporation-inhibiting high molecular sheet 51 is provided with a thin film sheet type absorbing material 52 on one surface thereof and an adhesive layer 53 is formed. The absorbing material 52 is adhered to a portion of the body perspiring a large amount of sweat, such as a forehead (edge of growing hairs) and a side, as shown in FIG. 5(B).

In this instance, a portion of the body to which the absorbing material 52 is adhered is preferably cleaned previously by, for example, washing. In addition, to achieve perspiration, an appointed amount of movement is done by the body or a temperature within a room is heightened. Thus, perspiration of sweat is promoted to obtain the appointed amount of sweat in a short time.

According to the above described method, a small quantity of sweat can be measured and advantages are achieved in that few instruments for obtaining the sample are required and a pretreatment is not required, which is different from the prior art 2 described above.

Although, in the above described preferred embodiments, fluids perspired from a living body, such as a human body, are the samples, an acidity of rain water and the like can also be measured, as shown in FIG. 6.

Figure 3A:
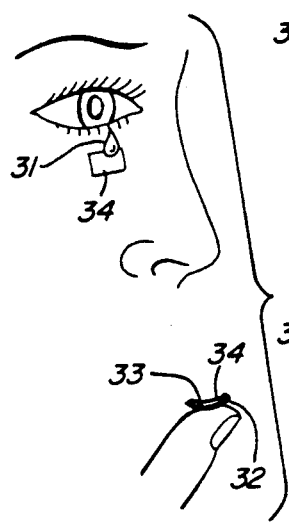
FIG. 3(A), (B), (C), (D), (E), (F) is a diagram showing a case where an ion-concentration of a tear is measured.
Figures 3B, 3C:
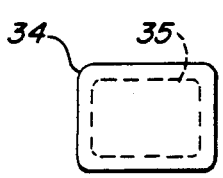
Figure 3D:
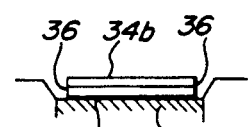
Figure 3E:
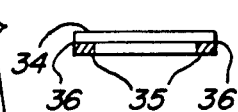
Figure 3F:
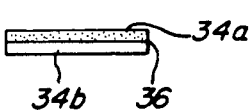

As shown in FIG. 6(A), a film 62 is affixed to a back surface of a thin film nonwoven sheet 61 being of several tens micron thick. A fixing frame 63, which is the same as the fixing frame 35 in FIG. 3(B), is provided, as well as an adhesive layer 64. The thin film nonwoven sheet 61 is affixed to an upper surface of a leaf 65 and taken off from the leaf 65 after a lapse of an appointed time beginning from a raining 66. The removed thin film nonwoven sheet 61 is then placed on the electrode 13 (14) to measure pH and the like.

Although, in the above described preferred embodiments, the sample is liquid, a relatively dry sample, such as skin and hair of a person, can also be measured.

Figure 7A:
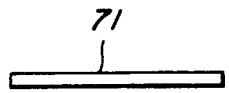
FIG. 7(A), (B), (C) is a diagram showing a case where an ion-concentration of skin and hair is measured.
Figure 7B:
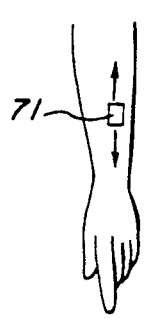
Figure 7C:
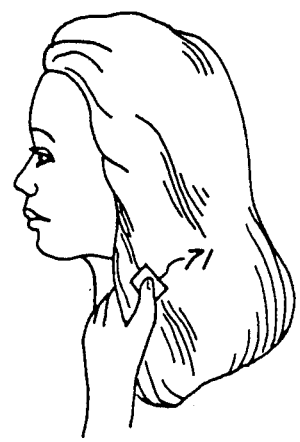

Referring to FIG. 7(A), reference numeral 71 designates an absorbing material previously impregnated with an appointed amount of distilled water or 0.1%-NaOH solution with HCl added so as to adjust pH to about 5.0. (The pH of a solution giving skin a minimum amount of swelling is about 5.0.) The resulting absorbing material 71 is sufficiently brought into contact with an appointed portion of a human arm [FIG. 7(B)] or hair [FIG. 7(C))]several times and then placed on the electrode 13 (14) to carry out an appointed measurement.

According to the present invention, an ion-concentration and the like in skin and hair having a low water-content can be simply measured, which is different from the prior art 3. In addition, the liquid which emanates no interferential ingredient is not limited to the above described distilled water and the like.

Sampling by previously impregnating an absorbing material with a solution emanating no interferential ingredient, as in the above described preferred embodiment, can also be applied to a deterioration test of iron and steel subjected to a pretreatment for painting, painting of cars, painting of buildings, plated articles and the like.

Although it is not shown in the drawings, a thin film absorbing sheet impregnated with an appointed quantity of distilled water is brought into contact with a surface of painted articles, plated articles and the like to achieve an appointed sampling. Then, the thin film absorbing sheet is placed on the electrode 13 (14), to measure pH, pNa, pCl, conductivity and the like at the same time.

In this case, an infinitesimal quantity of distilled water as the non-interferential liquid, about several microliters to 100 microliters, is sufficient. Advantages are achieved in that the dilution of a sample with a great quantity of water is not required, and the application of heat and the like to substances stuck to the surface is not required. Thereby, highly accurate measurements can be simply achieved without requiring any other treatments and the measurements over large items can be achieved at the same time.

A method according to the present invention can also be applied to the measurement of electrolytes and the like in foodstuffs such as fish, cows, pigs, and chickens.

Figure 8A:
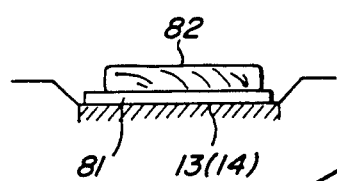
FIG. 8(A), (B), (C) is a diagram showing a case where an ion-concentration of fish is measured.
Figure 8B:
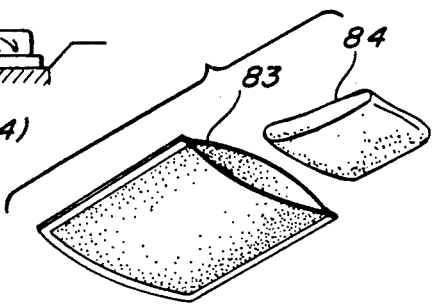
Figure 8C:
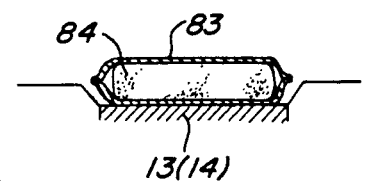

FIG. 8 shows a method of measuring an ion-concentration of fish. A comparatively dry portion, such as a surface, is measured in the following manner, as shown in FIG. 8(A). A sheet 81 formed of an absorbing material impregnated with distilled water is placed on the electrode 13 (14). A sample 82 composed of an appointed portion of fish is placed on the sheet 81. On the other hand, in the measurement of a comparatively wet portion, it is preferable that a sample 84 is put in a bag-like absorbing sheet 83 [FIG. 8(B)] and the absorbing sheet 83 is subjected to an appointed absorption [FIG. 8(C)].

Figure 9A:
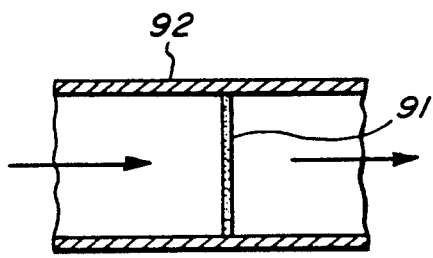
FIG. 9(A), (B) is a diagram showing a case where electrolytes in floating substances within a clean room are measured.

FIG. 9 shows a case where electrolytes in floating substances within a clean room are measured. A filter member 91 (such as filter paper, sponge and porous material) formed of a material eluting no electrolytes is impregnated with distilled water. The filter member 91 is set in a gas passage 92 for an appointed time and then the filter member 91 is placed on the electrode 13 (14) to carry out an appointed measurement.

According to this method, pNa, pCl and the like in the floating substances within a clean room can be simply measured.

Figure 9B:
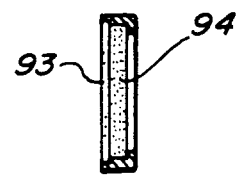
Figure 10A:
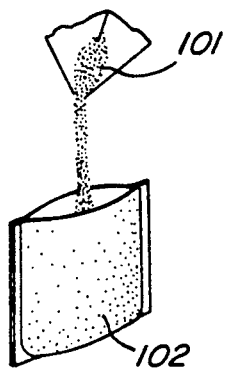
FIG. 10(A), (B), (C), (D) is a diagram showing a case where electrolytes in soil, ash and other powdery samples are measured.
Figure 10B:
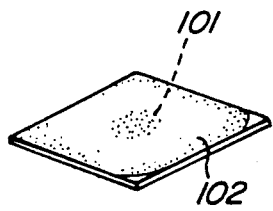
Figure 10C:
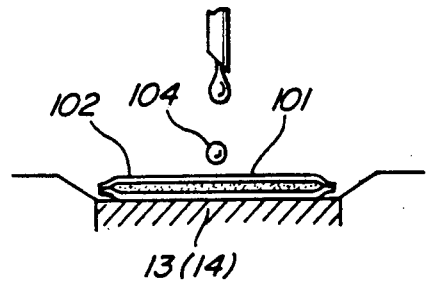
Figure 10D:
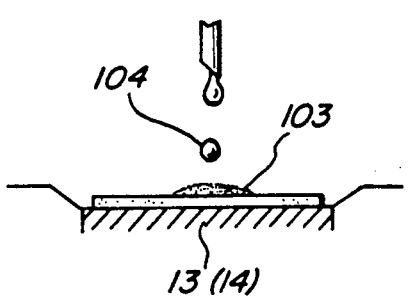

In addition, as shown in FIG. 9(B), a mesh of the above described filter member 91 is suitably selected according to a flow rate of gas. Only a first layer may be composed of a filter 93 formed of an absorbing material and the rest may be composed of a conventional gas filter 94 to form a composite filter.

FIG. 10 shows a method of measuring electrolytes in soil, ash and other powdery samples. In FIG. 10(A), a sample 101, such as soil, is housed in a bag 102 formed of an absorbing material. Then, a mouth portion of the bag 102 is sealed [FIG. 10(B)]. Subsequently, the bag 102, including the sample 101 therein, is placed on the electrode 13 (14) and distilled water 104 is added on the bag 102 drop by drop [FIG. 10(C)]. Alternatively, as shown in FIG. 10(D), a sheet-like absorbing material 103 is placed on the electrode 13 (14) and the sample 101 is placed on the sheet-like absorbing material 103. Further, distilled water 104 is added on the sample 101 drop by drop.

Figure 11:
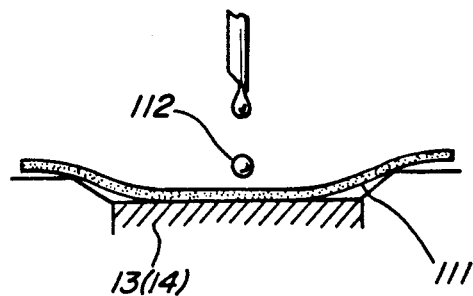
FIG. 11 is a diagram showing a case where an ion-concentration of cloth is measured.

In each of the above described preferred embodiments, the absorbing material has been composed of chemically stabilized materials eluting only a small amount of electrolyte within an error of measurement even though it is immersed in distilled water or a solution. However, as to substances eluting electrolytes to some extent when distilled water is added on it drop by drop as a sample, such as cloths, acidic papers and ceramics, a sample 111 (for example, a part of cloths) is directly placed on the electrode 13 (14) and distilled water is added on the sample 111 drop by drop to carry out an appointed measurement, as shown in FIG. 11.

The preferred embodiments of a calibrating sheet as well as a calibrating method for a measuring device for ion-concentration and the like will be described below with reference to FIGS. 12 to 14.

Figure 12:
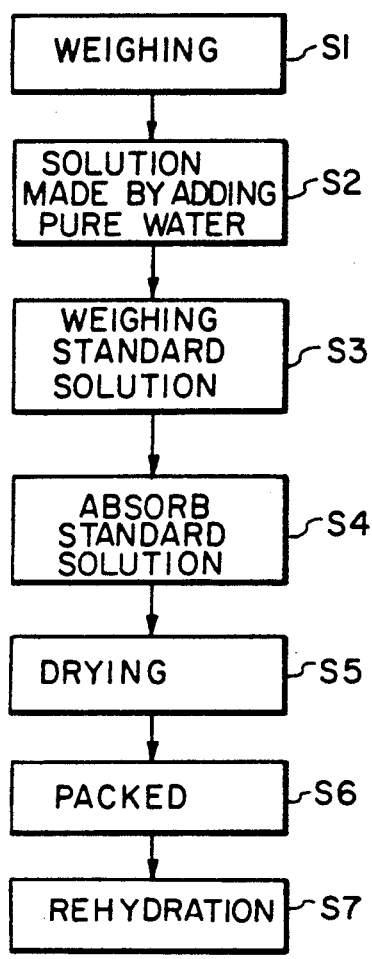
FIG. 12 is a chart showing individual steps from the manufacture of a sheet for use in a calibration according to the present invention to the calibration by the use of the sheet.
Figure 13:
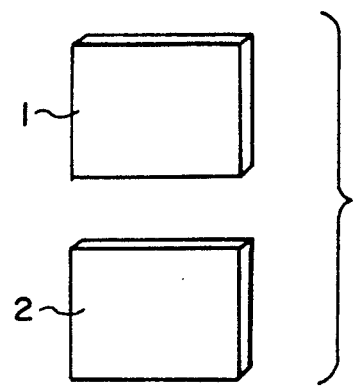
FIG. 13 is a perspective view showing one example of the sheet for use in the calibration.

FIG. 12 shows individual steps from the manufacture of the sheet for use in the calibration, according to the present invention, to the calibration by the use of the sheet. The sheets for use in the calibration of pH 4 and pH 7 will be illustrated.

First, 10.21 g of potassium hydrogen phthalate (JIS K8809, for use in the measurement of pH), 3.40 g of monopotassium phosphate (JIS K9007, for use in the measurement of pH), and 3.55 g of disodium phosphate (JIS K9020, for use in the measurement of pH) are weighed (refer to S1).

Subsequently, the above potassium hydrogen phthalate is dissolved in pure water (hereinafter referred to as "pure water for use in the preparation") have a conductivity of $2 \times 10^{-6} \Omega^{-1} cm^{-1}$ (at 25° C.) or less to prepare a phthalate standard solution of 1 liter. The above monopotassium phosphate and the above disodium phosphate are dissolved in pure water for use in the preparation to prepare a neutral phosphate standard solution of 1 liter (refer to S2).

Then, the phthalate standard solution and the neutral phosphate standard solution are weighed, respectively, and put in a separate vessel in an appointed quantity (refer to S3).

Subsequently, an absorbing sheet is immersed in the standard solution within the above vessel to absorb the solution in the absorbing sheet (refer to S4).

Chemically stabilized hygroscopic materials eluting no ion are preferably used as materials for the absorbing sheet. For example, high molecular materials having good flexibility and good adhesion to an electrode, in addition to the above described properties, and inorganic materials, glass fiber and ceramic fiber, may be used.

In the present preferred embodiment, a nonwoven fabric (of about 220 microns thick) formed of cellulose at the rate of 100% was used as the absorbing sheet.

Subsequently, the absorbing sheet impregnated with the standard solution is dried at room temperature to obtain a sheet for use in calibrations 1, 2 of pH 4 and pH 7 (refer to S5 and FIG. 13).

At this time, it is important to dry the sheet so that dried ingredient fine particle powders may not be torn off from the absorbing sheet after the evaporation of water.

The sheets for use in the calibrations 1, 2, which were obtained in the above described manner, are suitably packaged and preserved (refer to S6). In addition, these sheets for use in the calibrations 1, 2 are on the market as accessories of the pH meter in the form of a set, together with sheets used in calibration which are impregnated with other standard solutions.

Figure 14:
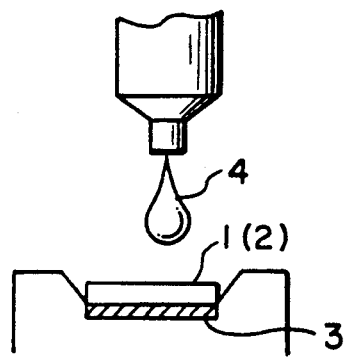
FIG. 14 is a diagram describing a method of calibrating an ion-concentration (and the like) measuring device.
Figure 15:
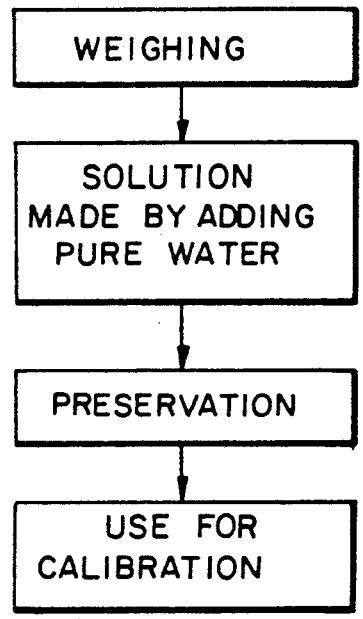
FIG. 15 is a chart describing the prior art.

To calibrate an electrode of the pH meter in the measurement of pH, as shown in FIG. 14, the sheet for use in the calibration 1 (2) is placed on a surface of a pH electrode 3 having flat surface construction, as shown, for example, in Japanese Patent Application No. Sho 61-285371 by the present assignee (Horiba, Ltd.), see U.S. Pat. No. 4,816,132. It is placed in a closely adhered manner, and pure water (of a quantity corresponding to a quantity of pure water for use in the preparation used in the preparation of the standard solution by adding pure water as shown by S2 in FIG. 12) is added on the sheet for use in the calibration 1 (2) drop by drop. This addition of pure water 4 drop by drop leads to the reformation of the standard solution as before the dehydration in the sheet, and the calibration of a pH electrode can be carried out by the use of this standard solution (refer to S7).

The pH electrode 3 of flat surface construction was calibrated by the use of the sheet for use in the calibration and the sheet was obtained by impregnating the absorbing sheet made of a nonwoven fabric formed of cellulose at the rate of 100% used in the present preferred embodiment with the above described standard solution. The sheet had good reproducibility and good reproducibility after leaving it unattended for several days.

In addition, in pH standard buffer solutions, the borate standard solution and the carbonate standard solution absorb carbon dioxide gas to remarkably lower pH according to circumstances. Therefore, in the case where the absorbing sheet is impregnated with these standard solutions to obtain the sheet for use in the calibration, it is preferable that a process of impregnating the absorbing sheet with the standard solution and the following processes are conducted in an atmosphere of inert gas. The dehydration as well as the preservation are also conducted so as to avoid contact with air.

In addition, in the case where the sheet for use in the calibration is prepared without using the pH standard buffer solution according to JIS, it is preferable that the absorbing sheet be impregnated with a quite novel buffer solution having an ingredient with a high buffering performance. Thus, an advantage occurs in that a suitable quantity of pure water can be added in the calibration.

In addition, the sheet for use in the calibration of the ion-concentration (and the like) measuring device, and the method of calibrating the ion-concentration (and the like) measuring device, according to the present invention, can be applied not only to the above described pH meter but also to general instruments in which various kinds of ion electrode, such as a pNa-sensor, pK-sensor, pCl-sensor, pCa-sensor and biosensor, are required to be calibrated by the use of a calibrating solution.

The electrode to be calibrated is not limited to the above described flat-shaped surface. The shapes of the conventional glass electrode, reference electrode, composite electrode and various kinds of ion electrode may be used. And, the present invention can be applied to the simplified calibration of an electrode of these ion-concentration measuring devices.

What is claimed is:

1. A method of calibrating an ion-concentration measuring device with an electrode, comprising the steps of:

providing a water-absorbing sheet of a chemically stabilized hygroscopic material that will not elute ions;

absorbing a calibrating solution of a predetermined concentration of pH calibrating material having a predetermined pH level into the sheet;

drying the water-absorbing sheet to leave it impregnated with the pH calibrating material from the calibrating solution;

bringing the water-absorbing sheet into contact with an electrode of the ion-concentration measuring device, and adding an appointed quantity of pure water drop by drop to the sheet to rehydrate the calibrating solution to the predetermined concentration to enable a pH calibration of the measuring device.

2. The method of claim 1 wherein the step of providing a water-absorbing sheet occurs in an inert atmosphere.

3. The method of claim 1 wherein the step of drying occurs in an inert atmosphere.

4. The method of claim 1 wherein the calibrating solution is selected from the group consisting of: 0.05 M-aqueous solution of potassium tetra oxalate $KH_3(C_2O_4)_2.2H_2O$, 0.05 M-aqueous solution of potassium hydrogen phthalate $C_6H_4$ (COOK) (COOH), 0.025 M-aqueous solution of mono potassium phosphate $KH_2PO_4$ and 0.025 M-aqueous solution of disodium phosphate $Na_2HPO_4$, 0.01 M-aqueous solution of sodium borate (borax) $Na_2B_4O_7.10H_2O$, and 0.025 M-aqueous solution of sodium hydrogen carbonate $NaHCO_3$ + 0.025 M-aqueous solution of sodium carbonate $Na_2CO_3$.

* * * * *